(12) United States Patent
Kennedy

(10) Patent No.: US 9,974,821 B2
(45) Date of Patent: May 22, 2018

(54) METHOD OF JUICING CANNABIS PLANT MATTER

(71) Applicant: Matthew Kennedy, Westminster, CA (US)

(72) Inventor: Matthew Kennedy, Westminster, CA (US)

(*) Notice: Subject to any disclaimer, the term of this patent is extended or adjusted under 35 U.S.C. 154(b) by 279 days.

(21) Appl. No.: 15/081,837

(22) Filed: Mar. 25, 2016

(65) Prior Publication Data

US 2017/0274028 A1    Sep. 28, 2017

(51) Int. Cl.
*A61K 36/00* (2006.01)
*A61K 36/185* (2006.01)

(52) U.S. Cl.
CPC ........ *A61K 36/185* (2013.01); *A61K 2236/13* (2013.01); *A61K 2236/15* (2013.01); *A61K 2236/39* (2013.01)

(58) Field of Classification Search
CPC ...................................................... A61K 36/00
USPC ......................................................... 424/725
See application file for complete search history.

(56) References Cited

U.S. PATENT DOCUMENTS 8,778,481 B2    7/2014    Bisterfeld Von Meer

*Primary Examiner* — Michael V Meller
(74) *Attorney, Agent, or Firm* — Christopher Pilling

(57) ABSTRACT

A method is provided, comprising steps: (a) harvesting *cannabis* plant matter predetermined time; (b) grinding the *cannabis* plant matter; (c) inserting the ground *cannabis* plant mater into a mesh filter bag; (d) pressing the mesh filter bag via a hydraulic press at a first speed and a first pressure, wherein the ground *cannabis* plant matter is separated into *cannabis* pulp and *cannabis* juice; and (e) collecting the *cannabis* juice for consumption.

10 Claims, 4 Drawing Sheets

METHOD OF JUICING CANNABIS PLANT MATTER

CROSS-REFERENCE TO RELATED APPLICATIONS

N/A

BACKGROUND OF THE INVENTION

1. Field of the Invention

The present invention relates to method of juicing *cannabis* plant matter, and more particular a method of juicing *cannabis* plant matter using a hydraulic cold-press machine.

2. Description of Related Art

*Cannabis* as a health supplement has been practiced for over 1,000 years. Traditionally *cannabis* is heated to release cannabinoids, primary tetrahydrocannabinol (THC) and cannabidiol (CBD). These cannabinoids are known to have many therapeutic and medical benefits. Additionally, *cannabis* in its natural form is a nutrient rich supplement comprising essential fatty acids, aminoacids, fibers, enzymes, vitamins, and minerals. Furthermore, *cannabis* in its natural form comprises tetrahydrocannabinol acid (THCA) and cannabidiol acid (CBDA), which are non-psychoactive cannabinoids providing anti-inflammatory, neuroprotective, anti-emetic, and anti-proliferative properties. Consequently, there is a need for an efficient and optimal method for allowing the intake of *cannabis* in its natural form to gain the benefits without providing a psychoactive effect.

BRIEF SUMMARY OF THE INVENTION

In one embodiment of the present invention a method is provided, comprising steps (a) harvesting *cannabis* plant matter at a predetermined time; (b) grinding the *cannabis* plant matter; (c) inserting the ground *cannabis* plant mater into a mesh filter bag; (d) pressing the mesh filter bag via a hydraulic press at a first speed and a first pressure, wherein the ground *cannabis* plant matter is separated into *cannabis* pulp and *cannabis* juice; and (e) collecting the *cannabis* juice for consumption.

In one embodiment, in step (a), the *cannabis* plant matter comprises organically grown leafy *cannabis* including *cannabis* leaves and *cannabis* stems. In one embodiment, the predetermined time is before the *cannabis* flowers form. In another embodiment, the organically grown leafy *cannabis* is harvested as a single plant to reduce handling and minimize oxidation prior to step (b). In one embodiment, in step (b), the *cannabis* plant matter is ground using a grinder having a blade length of ¼", wherein the blade is rotated at a maximum speed of 2400 revolutions per minute to avoid the *cannabis* plant matter from being heated to a predetermined temperature. In yet another embodiment, the *cannabis* plant matter comprises tetrahydrocannabinol acid (THCA), and the predetermined temperature is below a temperature threshold preventing the tetrahydrocannabinol acid from being converted into tetrahydrocannabinol (THC) and minimizing nutrient degradation. In one embodiment, in step (c), the mesh filter bag comprises openings having a size of 400 to 600 microns. In one embodiment, in step (d), the ground *cannabis* plant matter comprises tetrahydrocannabinol acid (THCA), and the first speed is set to a first maximum level and the first pressure is set to a second maximum level to avoid the ground *cannabis* plant matter from reaching a temperature threshold preventing the tetrahydrocannabinol acid from being converted into tetrahydrocannabinol (THC) and minimizing nutrient degradation. In another embodiment, the second maximum level is 1800 pounds per square inch. In yet another embodiment, a further step is provided, wherein the *cannabis* pulp is mixed in the mesh filter bag and the mesh filter bag is pressed again to extract additional *cannabis* juice from the *cannabis* pulp. In one embodiment, in step (e), the consumption of the *cannabis* juice does not cause a psychoactive effect.

In another aspect of the invention, a method is provided, comprising steps (a) harvesting *cannabis* plant matter, wherein the *cannabis* plant matter comprises *cannabis* leaves and *cannabis* stems; (b) washing and rinsing the *cannabis* plant matter; (c) grinding the *cannabis* plant matter; (d) inserting the ground *cannabis* plant mater into a mesh filter bag; (e) pressing the mesh filter bag via a hydraulic press at a first speed and a first pressure, wherein the ground *cannabis* plant matter is separated into *cannabis* pulp and *cannabis* juice; and f) collecting the *cannabis* juice for consumption, wherein the consumption of the *cannabis* juice does not cause a psychoactive effect.

In one embodiment, in step (a), the *cannabis* plant matter does not include *cannabis* flowers. In another embodiment, a further step is provided, wherein the *cannabis* pulp is mixed in the mesh filter bag and the mesh filter bag is pressed again to extract additional *cannabis* juice from the *cannabis* pulp.

BRIEF DESCRIPTION OF THE SEVERAL VIEWS OF THE DRAWINGS

Other features and advantages of the present invention will become apparent when the following detailed description is read in conjunction with the accompanying drawings, in which.

DETAILED DESCRIPTION OF THE PREFERRED EMBODIMENT

The following description is provided to enable any person skilled in the art to make and use the invention and sets forth the best modes contemplated by the inventor of carrying out their invention. Various modifications, however, will remain readily apparent to those skilled in the art, since the general principles of the present invention have been defined herein to specifically provide a method of juicing *cannabis* plant matter.

The *cannabis* plant matter comprises many cannabinoids in its natural state, i.e. raw, including but not limited to tetrahydrocannabinol acid (THCA), cannabidiol acid (CBDA), cannabichromne acid (CBCA), and cannabigerolic acid (CBGA) which have many medicinal properties attributed to them. For instance, TCHA and CBDA may be used to reduce inflammation, inhibit cell growth in tumors and cancer cells, and also suppress muscle spasms. Likewise, CBCA and CBGA may be used to kill or slow bacteria growth, treat fungal infections, and release pain.

Figure 1:
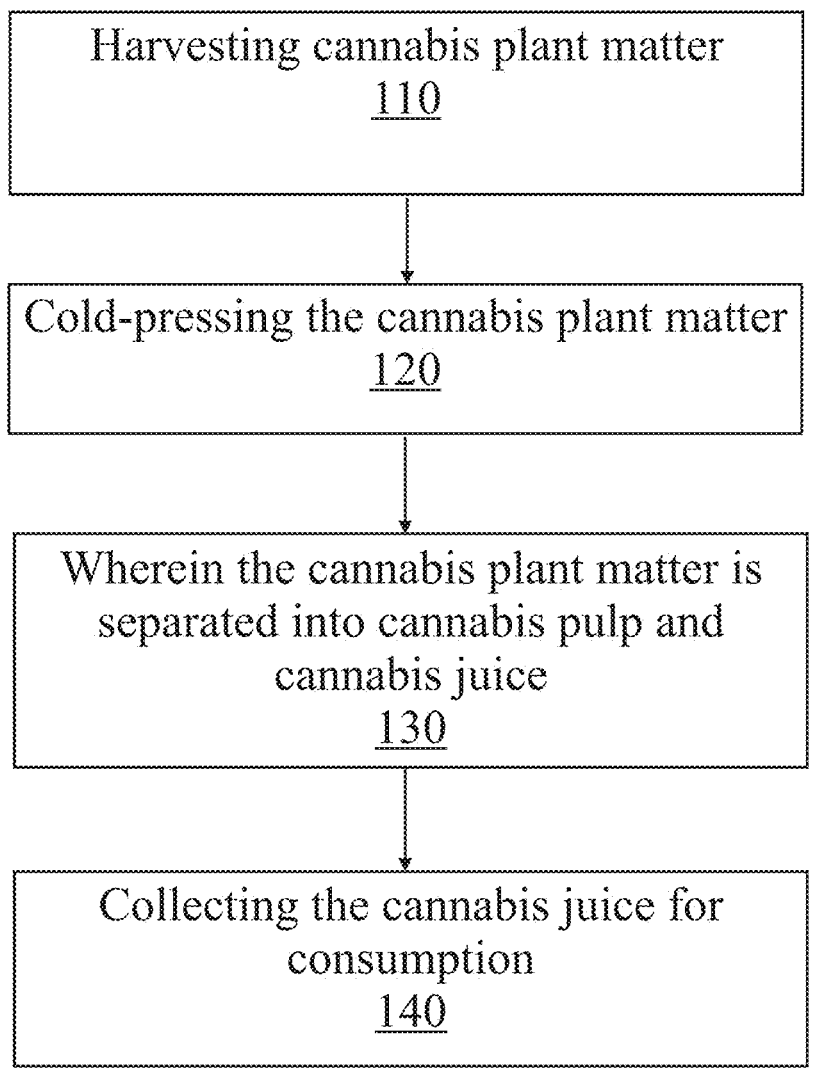
FIG. 1 is a method of juicing *cannabis* plant matter according to an embodiment of the present invention.

FIG. 1 is a method 100 of juicing *cannabis* plant matter according to an embodiment of the present invention. Referring now to FIG. 1, in step 110, *cannabis* plant matter is harvested. In step 120, the *cannabis* plant matter is cold-pressed. Any commercial cold-press juicer may be used, which relies on a hydraulic press. The details of the cold-press, as well as the specific setting of the hydraulic press, such as press speed and pressure will be discussed in greater detail below. In step 130, the *cannabis* matter is separated in *cannabis* pulp and *cannabis* juice. In step 140, the *cannabis* juice is collected for consumption. The *cannabis* juice is the desired result of the method, and may be consumed to take advantages of medicinal properties of the plant, including but not limited to anti-inflammatory, neuroprotective, anti-emetic, and anti-proliferative properties, as well as the nutrients, essential fatty acids, aminoacids, fibers, enzymes, vitamins, and minerals.

Figure 2:
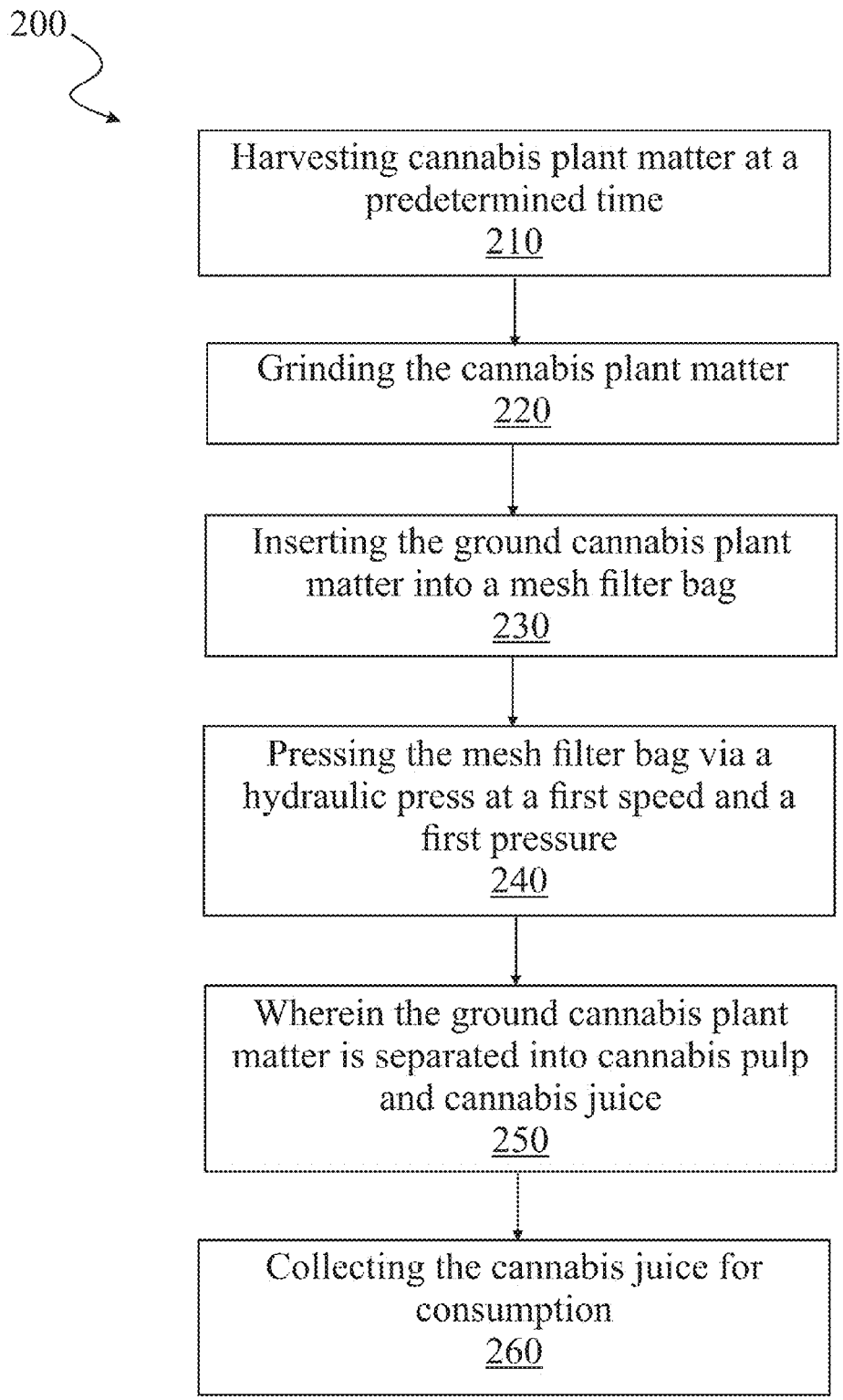
FIG. 2 is a method of juicing *cannabis* plant matter according to an embodiment of the present invention.

FIG. 2 is a method 200 of juicing *cannabis* plant matter according to an embodiment of the present invention. Referring now to FIG. 2, in step 210, *cannabis* plant matter is harvested at a predetermined time. In some embodiments, the *cannabis* plant matter comprises *cannabis* leaves and stems. Traditionally, *cannabis* plants are harvested exclusively for their flowers, and *cannabis* flowers have an ideal maturity date which varies by *cannabis* variety, including but not limited to *cannabis sativa* and *cannabis indica*. Depending on the variety, the harvesting time may be between 8 to 11 weeks. During this harvesting time, and sometimes a week or two prior, the *cannabis* leaves start showing signs of nutrient deficiency as the *cannabis* plant needs all of its available nutrients to support the *cannabis* flowers. In some embodiments, it is a particular advantage of the present invention to harvest the *cannabis* plant before the *cannabis* flowers form. This allows the whole leafy *cannabis* plant to be harvested without harvesting the *cannabis* leaves and stems separately from the flowers. Furthermore, by harvesting the entire leafy *cannabis* plant it reduces the amount of handling and also minimizes the amount of oxidation that occurs after harvesting, as the *cannabis* plant matter is exposed to air. Oxidation causes the *cannabis* plant matter to be subject to nutrient degradation, thus it is a goal to limit oxidation prior to juicing. In alternative embodiments, the *cannabis* plant matter is harvested during the vegetation stage, prior the flowing stage allowing for the whole leafy *cannabis* plant to be harvested prior to flower development. The *cannabis* plant matter may be either from a male or female *cannabis* variety. Another particular advantage of harvesting the *cannabis* plant before the *cannabis* flowers form is that more *cannabis* plants may be grown in a shorter amount of time, as the growing cycle is reduced. This allows *cannabis* plant farmers to maximum crop yields. It is also critical that the harvested *cannabis* plant matter be free of any pesticides and be from organically grown *cannabis* plants. This ensures the *cannabis* is safe for consumption.

Still referring to FIG. 2, in step 220, the *cannabis* plant matter is grinded. The grinding allows for the maximum amount of plant matter to be juiced, and more specifically increases the amount of surface area of plant matter increasing efficiency. In some embodiments, the *cannabis* plant matter is ground using a grinder having a blade length of ¼". This blade may be of any shape, but is preferably constructed of a circular shape. It is also critical that the grinder is attached to the juicing apparatus to limit handling to prevent possible contamination from the operators. The juicing apparatus will be discussed in greater detail below. In some embodiments, the blade is rotated at a maximum speed of 40 hertz or 2400 revolutions per min (RPM). This speed avoids heating the *cannabis* plant matter to a point where possible reactions may occur, including but not limited to nutrient degradation and acid cannabinoids being converting to non-acid cannabinoids which may lead to psychoactive effects for the consumer. For instance, during operation if the temperature of the *cannabis* plant matter reaches a temperature threshold a portion of the tetrahydrocannabinol acid (THCA) and cannabidiol acid (CBDA) may be converted into tetrahydrocannabinol (THC) and cannabidiol (CBD) respectively.

In step 230, the ground *cannabis* plant matter is inserted into a mesh filter bag. In some embodiments, the grinder is a hopper style grinder allowing the ground *cannabis* plant matter to fall directly into the mesh bag. This is particularly advantageous as it reduces the handling of the fresh plant matter maintaining optimally cleanliness. The mesh filter bag comprises openings having a size of 400 to 600 microns. It should be understood that the openings are not limited to the aforementioned sizes, and optimum sizes may be discovered by routine experimentation. After pressing, which will be discussed in greater detail below, the mesh filter bag is designed to retain the pulp while allowing the juice to pass through the openings. Next, in step 240, the mesh filter bag is pressed via a hydraulic press at a speed and a pressure. As previously mentioned, heating the *cannabis* plant matter to a point where possible reactions may occur, including but not limited to nutrient degradation and acid cannabinoids being converting to non-acid cannabinoids which may lead to psychoactive effects for the consumer is not desired. Consequently, the speed and pressure must not allow the *cannabis* plant matter to be heating above a threshold temperature where the possible reactions may occur. The pressure increases when the ground *cannabis* plant matter is actively being pressed between plates operated via the hydraulic press. The maximum pressure is 1800 pounds per square inch (PSI). Pressing at a slow speed and not exceeding the maximum pressure allows for the maximum amount of juice to be extracted without causing possible reactions.

In step 250, the ground *cannabis* matter is separated in *cannabis* pulp and *cannabis* juice. Last, in step 260, the *cannabis* juice is collected for consumption. The *cannabis* juice is the desired result of the method, and may be consumed to take advantages of medicinal properties of the plant, including but not limited to anti-inflammatory, neuroprotective, anti-emetic, and anti-proliferative properties, as well as the nutrients, essential fatty acids, aminoacids, fibers, enzymes, vitamins, and minerals.

Figure 3:
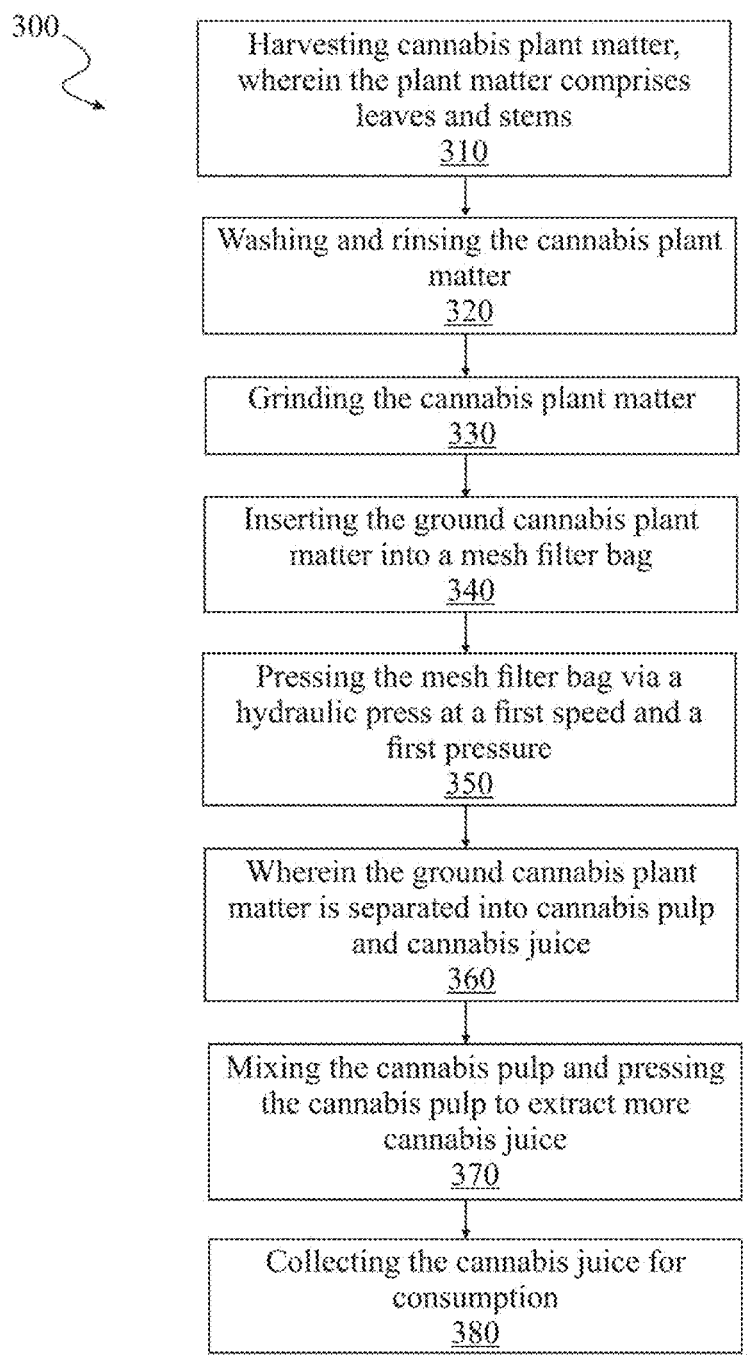
FIG. 3 is a method of juicing *cannabis* plant matter according to an embodiment of the present invention.

FIG. 3 is a method 300 of juicing *cannabis* plant matter according to an embodiment of the present invention. Referring now to FIG. 3, in step 310, *cannabis* plant matter is harvested. In some embodiments, the *cannabis* plant matter comprises *cannabis* leaves and stems. In some embodiments, the *cannabis* plant matter does not include *cannabis* flowers and ideally the *cannabis* plant matter is harvested from single whole leafy *cannabis* plants. In step 320, the *cannabis* plant matter is washed and rinsed prior to juicing. This is an optional step, as the *cannabis* plant matter and whole leafy *cannabis* plants should be organically grown, however the *cannabis* plant matter may be washed and rinsed to remove any potential containments, bugs, dirt, and dust off prior to juicing. Next, in step 330, the *cannabis* plant matter is grinded. It is critical that the grinder is attached to the juicing apparatus to limit handling to prevent possible contamination from the operators. It is also critical that the grinding speed avoids heating the *cannabis* plant matter to a point where possible reactions may occur, including but not limited to nutrient degradation and acid cannabinoids being converting to non-acid cannabinoids which may lead to psychoactive effects for the consumer.

In step 340, the ground *cannabis* plant matter is inserted into a mesh filter bag. In some embodiments, the grinder is a hopper style grinder allowing the ground *cannabis* plant matter to fall directly into the mesh bag. This is particularly advantageous as it reduces the handling of the fresh plant matter maintaining optimally cleanliness. Next, in step 350, the mesh filter bag is pressed via a hydraulic press at a speed and a pressure. As previously mentioned, heating the *cannabis* plant matter to a point where possible reactions may occur, including but not limited to nutrient degradation and acid cannabinoids being converting to non-acid cannabinoids which may lead to psychoactive effects for the consumer is not desired. Consequently, the speed and pressure must not allow the *cannabis* plant matter to be heating about a threshold temperature where the possible reactions may occur. The pressure increases when the ground *cannabis* plant matter is actively being pressed between plates operated via the hydraulic press. The maximum pressure is 1800 pounds per square inch (PSI). Pressing at a slow speed while not exceeding the maximum pressure allows for the maximum amount of juice to be ex acted without causing possible reactions.

In step 360, the ground *cannabis* matter is separated in *cannabis* pulp and *cannabis* juice. Next, in step 370, the remaining *cannabis* pulp is mixed in the mesh filter bag and the mesh filter bag is pressed again to extract additional *cannabis* juice from the *cannabis* pulp. Last, in step 380, the *cannabis* juice is collected for consumption. The *cannabis* juice is the desired result of the method, and may be consumed to take advantages of medicinal properties of the plant, including but not limited to anti-inflammatory, neuroprotective, anti-emetic, and anti-proliferative properties, as well as the nutrients, essential fatty acids, aminoacids, fibers, enzymes, vitamins, and minerals.

Figure 4:
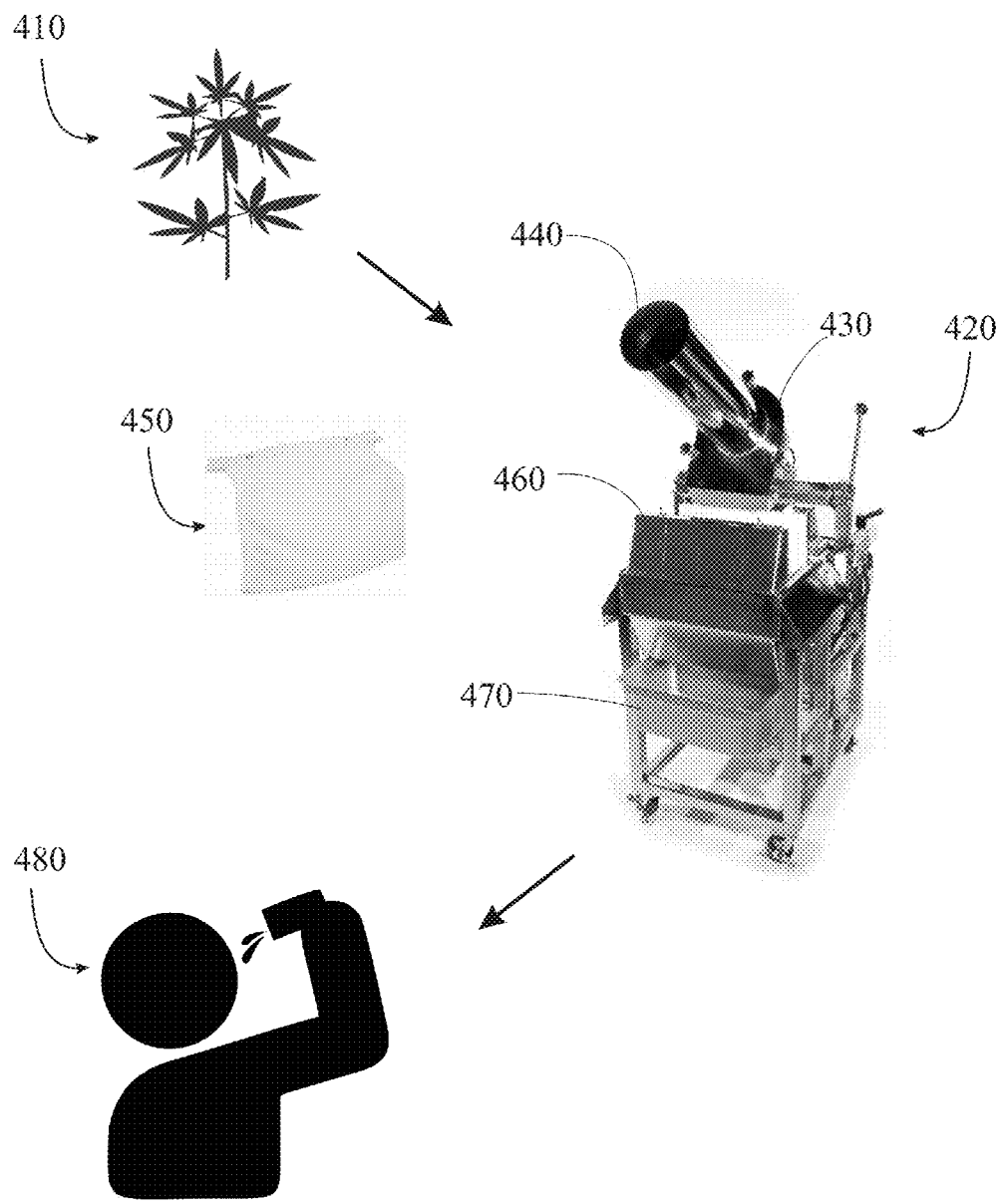
FIG. 4 is a diagram illustrating a method of juicing *cannabis* plant matter according to an embodiment of the present invention.

FIG. 4 is a diagram illustrating a method of juicing *cannabis* plant matter according to an embodiment of the present invention. In some embodiments, organic leafy *cannabis* plants 410 are grinded by a grinder 430, wherein the grinder is attached to a hydraulic press 420. The leafy *cannabis* plants and corresponding plant matter are feed into a hopper 440 which guides the plant matter into the grinder at a controlled speed as well known in the art. The ground plant matter is falls directly into a mesh filter bag 450 which is located between a pair of hydraulic press plates 460. The mesh filter bag has been removed from the hydraulic press for clarity. The hydraulic press is then activated, and the pair of hydraulic press plates crushes the ground plant matter located into the mesh filter bag separating e ground plant matter into a pulp and a juice. The pulp remains in the mesh filter bag, while the juice is collected in a container 470. The *cannabis* juice is then ready for consumption 480. In some embodiments, the *cannabis* juice is mixed with other juices, including but not limited to vegetable and fruit juices allowing for the *cannabis* juice to be more appetizing.

Although the invention has been described in considerable detail in language specific to structural features and or method acts, it is to be understood that the invention defined in the appended claims is not necessarily limited to the specific features or acts described. Rather, the specific features and acts are disclosed as exemplary preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. Such variations and alternate embodiments are contemplated, and can be made without departing from the spirit and scope of the invention.

In addition, reference to "first," "second," "third," and etc. members throughout the disclosure (and in particular, claims) are not used to show a serial or numerical limitation but instead are used to distinguish or identify the various members of the group.

What is claimed is:

1. A method for producing *cannabis* juice consisting essentially of:
   (a) harvesting *cannabis*;
   (b) grinding the *cannabis* to produce a ground *cannabis*;
   (c) inserting the ground *cannabis* into a mesh filter bag;
   (d) pressing the mesh filter bag via a hydraulic press at a first speed and a first pressure, wherein the ground *cannabis* in the mesh filter bag is separated into a *cannabis* pulp and a *cannabis* juice; and
   (e) separating out only the *cannabis* juice.

2. The method of claim 1, wherein in step (a), the *cannabis* is organically grown leaves and stems.

3. The method of claim 2, wherein the organically grown *cannabis* is a single plant to reduce handling and minimize oxidation prior to step (b).

4. The method of claim 3, wherein the *cannabis* is picked before flowers form on the *cannabis*.

5. The method of claim 1, wherein in step (b), the *cannabis* is ground using a grinder having a blade length of ¼" and wherein the blade is rotated at a maximum speed of 2400 revolutions per minute to prevent the *cannabis* from being heated to a predetermined temperature.

6. The method of claim 5, wherein the *cannabis* consists essentially of tetrahydrocannabinol acid, and the predetermined temperature is below a temperature threshold preventing the tetrahydrocannabinol acid from being converted into tetrahydrocannabinol and minimizing nutrient degradation.

7. The method of claim 1, wherein in step (c), the openings on the mesh filter bag are 400 to 600 microns.

8. The method of claim 1, wherein in step (d), the ground *cannabis* consist essentially of tetrahydrocannabinol acid and the first speed is set to a first maximum level and the first pressure is set to a second maximum level to avoid the ground *cannabis* from reaching a temperature threshold preventing the tetrahydrocannabinol acid from being converted into tetrahydrocannabinol and minimizing nutrient degradation.

9. The method of claim 8, wherein the second maximum level is 1800 pounds per square inch.

10. The method of claim 1, wherein the *cannabis* pulp is mixed in the mesh filter bag and the mesh filter bag is pressed again to extract additional *cannabis* juice from the *cannabis* pulp.

* * * * *